(12) United States Patent
Jones et al.

(10) Patent No.: US 9,339,788 B2
(45) Date of Patent: May 17, 2016

(54) ZEOLITES AND COMPOSITES INCORPORATING ZEOLITES

(76) Inventors: Susan Jones, Surrey (GB); Paul Sermon, Henley-on-Thames (GB)

( * ) Notice: Subject to any disclaimer, the term of this patent is extended or adjusted under 35 U.S.C. 154(b) by 120 days.

(21) Appl. No.: 14/128,313

(22) PCT Filed: Jun. 27, 2012

(86) PCT No.: PCT/GB2012/051506
§ 371 (c)(1),
(2), (4) Date: Jan. 24, 2014

(87) PCT Pub. No.: WO2013/001296
PCT Pub. Date: Jan. 3, 2013

(65) Prior Publication Data
US 2014/0141963 A1    May 22, 2014

(30) Foreign Application Priority Data

Jun. 27, 2011 (GB) .................................. 1110868.5

(51) Int. Cl.
| | | |
|---|---|---|
| *C01B 39/04* | (2006.01) | |
| *B01D 53/04* | (2006.01) | |
| *B01J 20/18* | (2006.01) | |
| *C01B 39/14* | (2006.01) | |
| *C01B 39/20* | (2006.01) | |
| *C01B 39/22* | (2006.01) | |
| *C01B 39/24* | (2006.01) | |
| *C01B 39/36* | (2006.01) | |
| *C01B 39/38* | (2006.01) | |
| *C01B 39/40* | (2006.01) | |
| *B01J 39/14* | (2006.01) | |
| *C07C 7/12* | (2006.01) | |
| *C07C 17/389* | (2006.01) | |

(52) U.S. Cl.
CPC ........ *B01J 20/18* (2013.01); *B01J 39/14* (2013.01); *C01B 39/04* (2013.01); *C01B 39/145* (2013.01); *C01B 39/20* (2013.01); *C01B 39/205* (2013.01); *C01B 39/22* (2013.01); *C01B 39/24* (2013.01); *C01B 39/36* (2013.01); *C01B 39/38* (2013.01); *C01B 39/40* (2013.01); *C07C 7/12* (2013.01); *C07C 17/389* (2013.01); *B01D 2253/25* (2013.01)

(58) Field of Classification Search
CPC .............. B01D 53/04; B01D 2253/108; B01D 2253/25; B01D 2257/2066; B01D 2257/406; B01D 2257/502; B01D 2257/504; B01D 2257/702; B01D 2257/80; B01J 20/18; B01J 39/14; C07C 17/389; C07C 7/12; C01B 39/04; C01B 39/145; C01B 39/20; C01B 39/205; C01B 39/22; C01B 39/24; C01B 39/36; C01B 39/38; C01B 39/40
USPC ................. 95/128, 131, 139, 140, 143, 117; 96/108, 154; 502/60, 68, 69, 77–79, 74
See application file for complete search history.

(56) References Cited

U.S. PATENT DOCUMENTS

| | | | |
|---|---|---|---|
| 5,425,934 A * | 6/1995 | Malla et al. .................... | 423/714 |
| 5,895,769 A * | 4/1999 | Lai ..................................... | 502/4 |
| 2002/0034471 A1 * | 3/2002 | Jacobsen et al. .............. | 423/700 |

OTHER PUBLICATIONS

Madsen et al., "Nanosized zeolite crystals—convenient control of crystal size distribution by confined space synthesis", (1999), Chem. Commun., pp. 673-674.*
Schmidt et al., "Confined Space Synthesis. A Novel Route to Nanosized Zeolites", (2000), Inorg. Chem. 39, pp. 2279-2283.*

* cited by examiner

*Primary Examiner* — Frank Lawrence
(74) *Attorney, Agent, or Firm* — Matthew G. McKinney, Esq.; Milbrath & Gilschrist, P.A.

(57) ABSTRACT

According to the invention there is provided a zeolite having a porous structure produced by forming the zeolite on a porous carbon substrate which has been substantially or completely removed, wherein (i) the zeolite was formed on the substrate at a loading of at least 8% by weight and/or (ii) the zeolite has a reinforcing layer.

8 Claims, 8 Drawing Sheets a) b)

a) A silica xerogel was assessed using SEM and b) EDX assessed before being used as a membrane to coat a MASTcarbonTM sphere c)

Silica coating onto a carbon sphere, coatings ranged between 350nm-3.2um a) b)

a) a PVA coated and carbonised zeolite pellet b) 2.5% PVA soln. carbon coating is 1um thick and a 1% PVA soln. 0.5um before carbonisation (see above film image).

c) but reduced to c. 23nm on carbonisation (see TGA analysis above).

a) Silica monolith from Left – Ludox/Ethanol, carbon sphere pore formers and Right Ludox/Ethanol, Ethyleneglycol pore formers, after burning away carbon/ethanol etc. and b) Ethanol/Ludox dipped carbon and Ludox only dried before carbon removal.

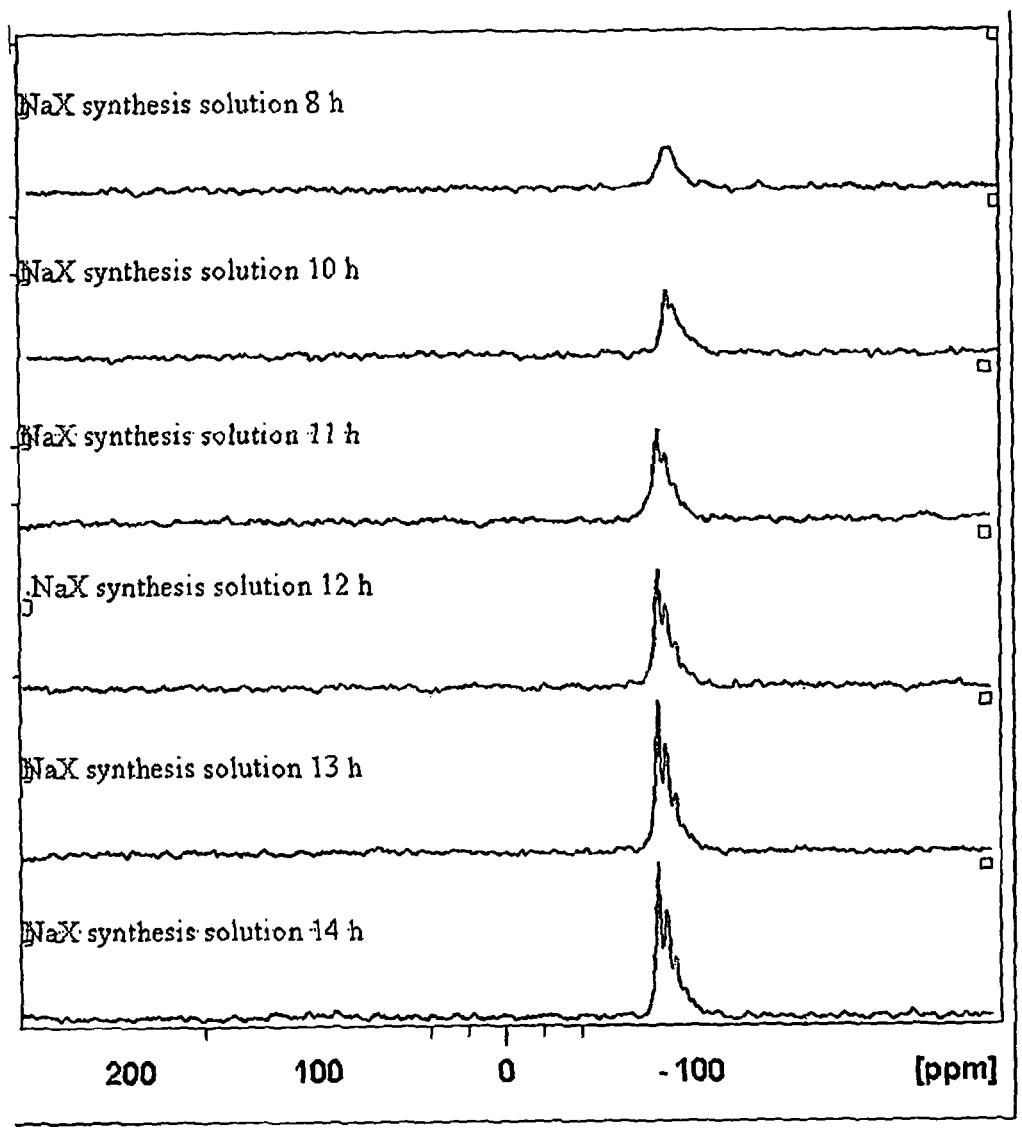
Figure 4. 29Si NMR evidence of NaX formation in C pores

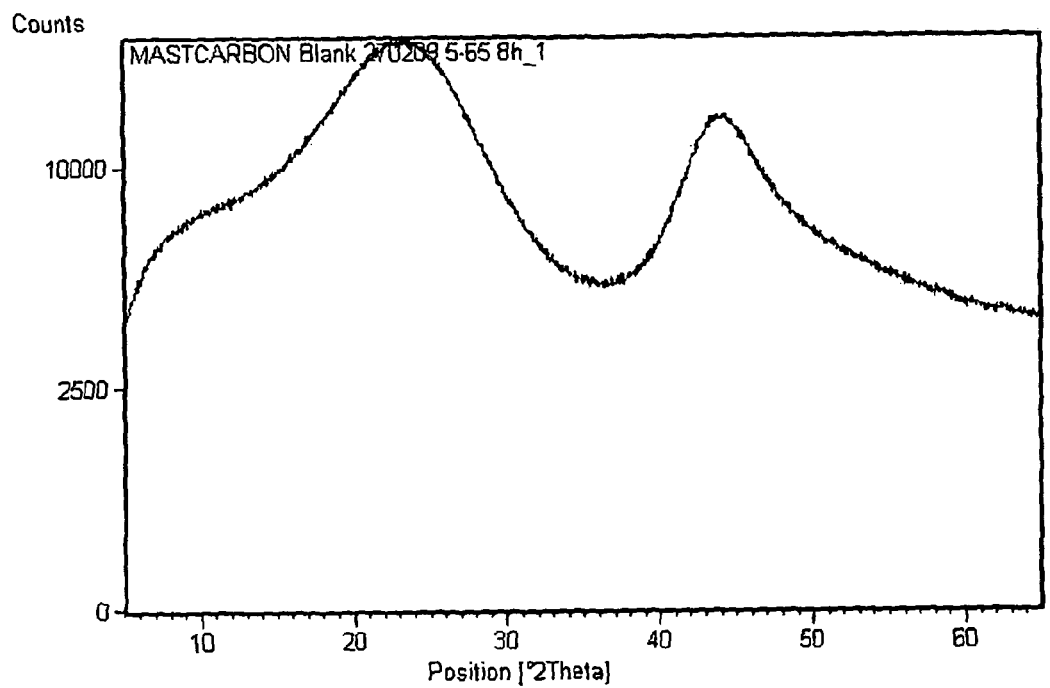
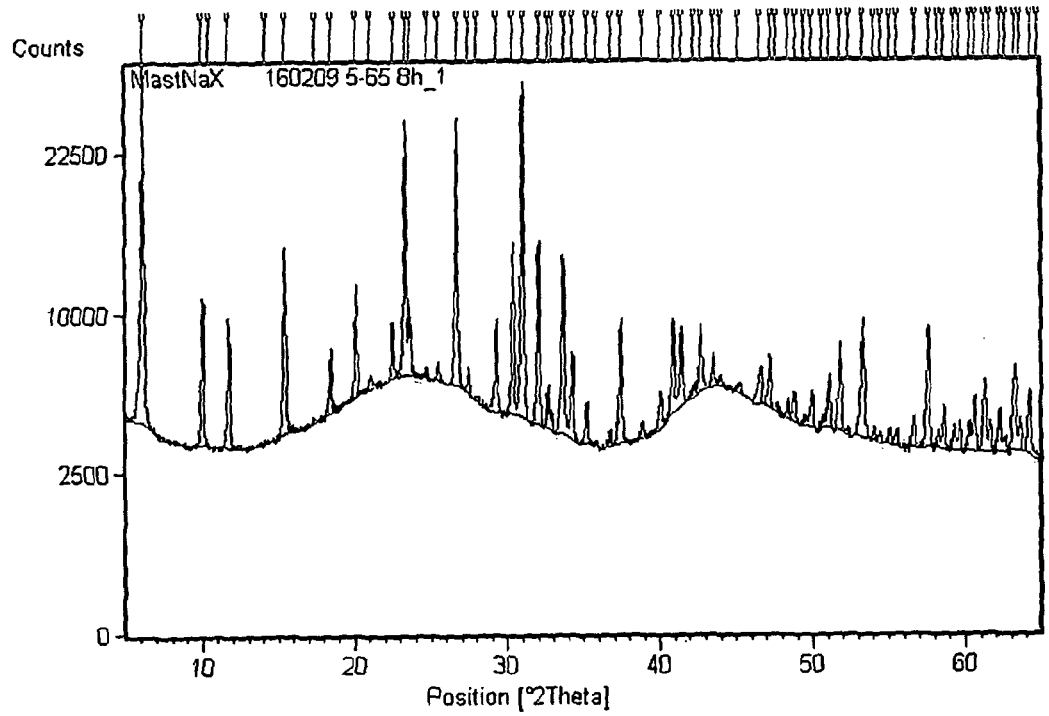
Figure 5. XRD of MastCarbon* carbon (a) and evidence of NaX zeolite formation in MastCarbon* carbon pores (b)

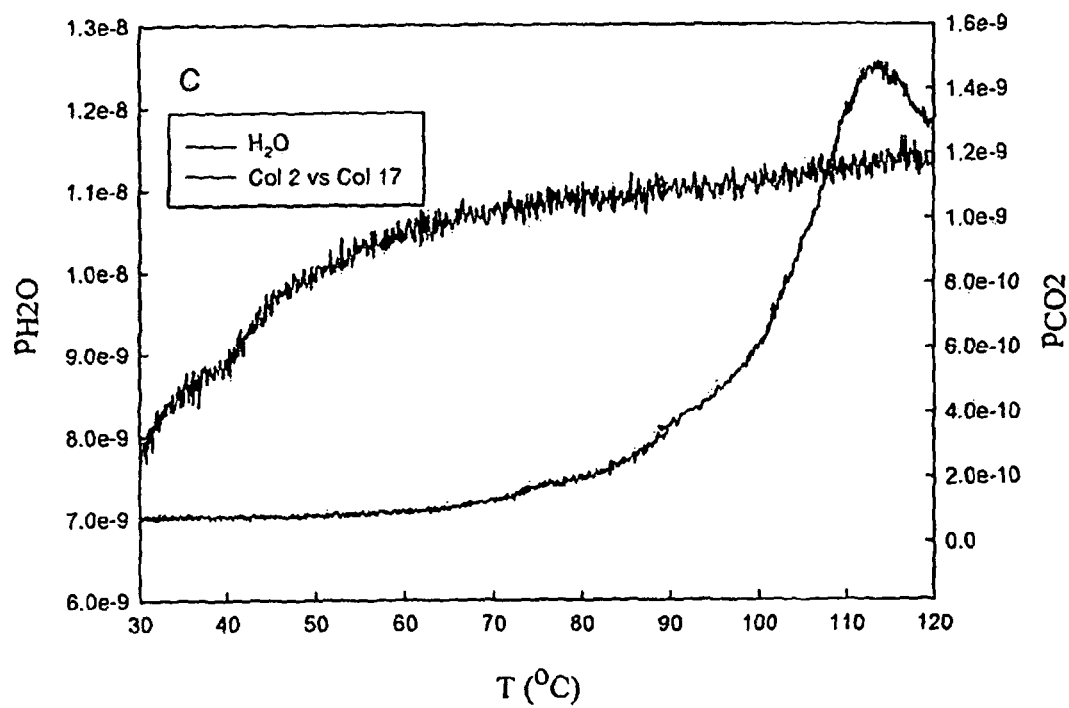
Figure 6. Temperature-programmed desorption of $CO_2$ and $H_2O$ from carbon

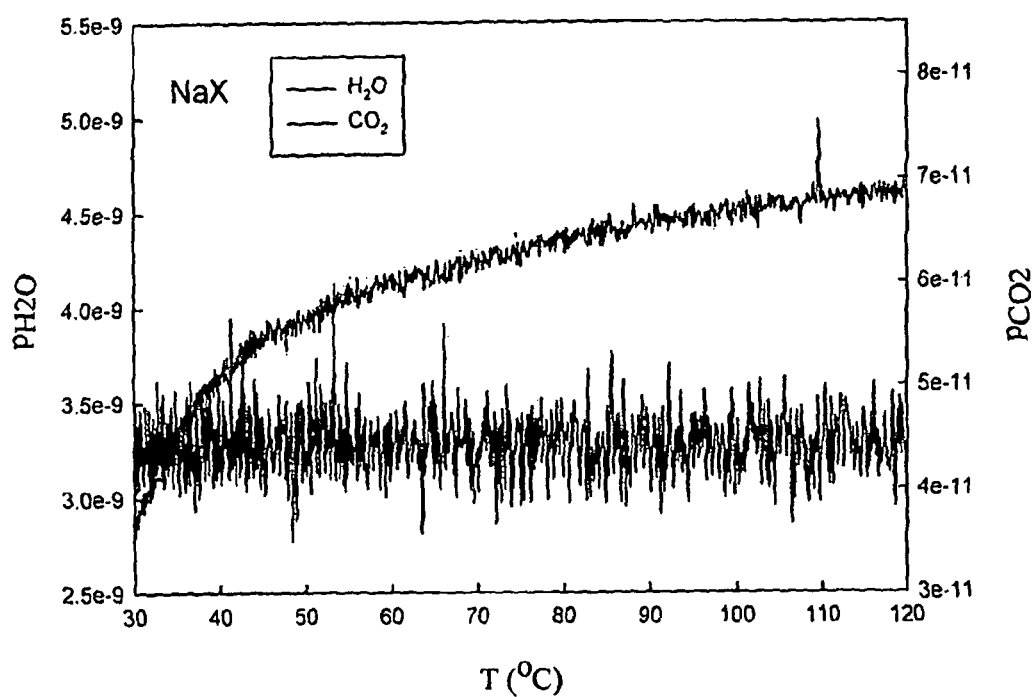
Figure 7. Temperature-programmed desorption of $CO_2$ and $H_2O$ from NaX

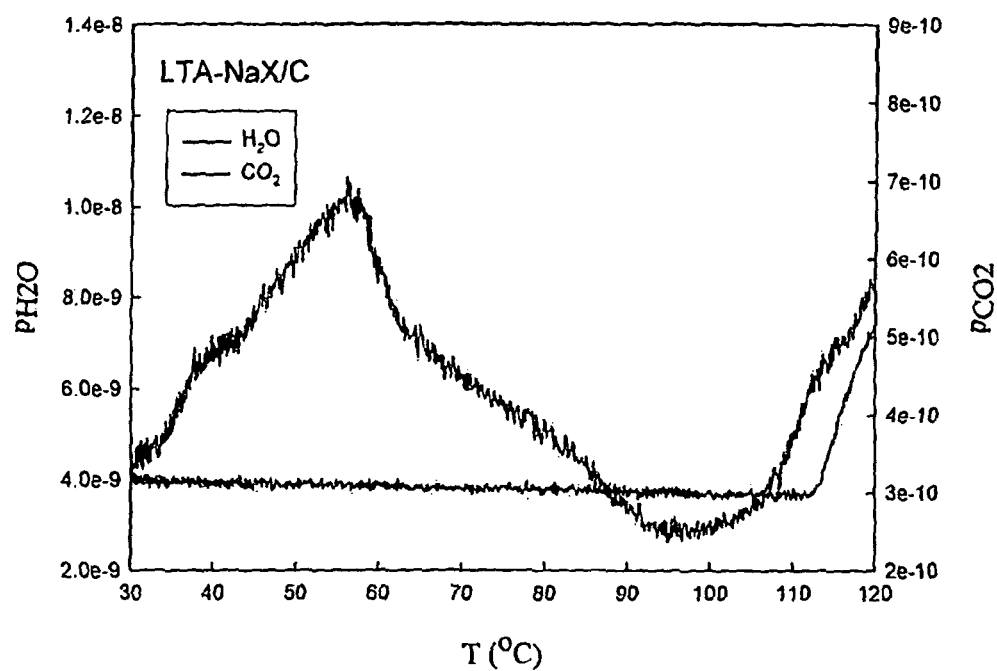
Figure 8. Temperature-programmed desorption of $CO_2$ and $H_2O$ from LTA-NaX/C

ZEOLITES AND COMPOSITES INCORPORATING ZEOLITES

This invention relates to zeolites and composites incorporating zeolites, with particular reference to composite materials which include one or more zeolites formed within or on a carbon substrate. The invention also relates to associated methods of manufacture and to uses of the zeolites and composites.

Zeolites are well known crystalline aluminosilicates. Zeolite molecular sieves are cheap, abundant and green materials which can be used as catalysts and/or ion exchangers. However, practical use can be problematic, because the small crystals sizes inhibit fluid transport. In order to overcome this problem, various approaches have been adopted. Attempts have been made to synthesise large crystals, but this involves the use of toxic chemicals, diffusion is compromised, and cracking of the zeolite crystals usually occurs on template removal. It is also known to pellet zeolites, but this increases production time and costs, and can interfere with adsorption. It is also known to grow zeolite films onto alumina, silica or metal substrates, but the dissolution of the substrate in the synthesising solution can lead to contamination or production problems and as metal substrates expand/contract on heating/cooling there is a risk of the zeolite film cracking and dislodging the zeolite crystals during utilization.

The inventors have developed an alternative route which involves synthesising zeolite in the pores of a carbon substrate, and some preliminary results are described in S H Jones, S Tennison, E Crezee, and P A Sermon, Preparation of Zeolite/Carbon Composites via LTA Zeolite Synthesis in Macropores of Unmodified Carbon Supports, Thirtieth National Conference on Advanced Ceramics and Composites, American Ceramics Society Conference Proceedings (2007). The preparation of a molecular sieve comprising a zeolite formed on activated carbon is discussed in U.S. Pat. No. 6,117,810. The inventor has now made certain improvements on the preliminary work which are the subject of the present application. The present invention, in at least some of its embodiments, provides improved composite materials, zeolites, methods of manufacture and uses thereof.

According to a first aspect of the invention there is provided a zeolite having a porous structure. It is understood that this porous structure of the zeolite corresponds to the porous structure of the carbon substrate, and is in addition to the usual nanoporous structure of a zeolite.

Earlier attempts to remove the carbon substrate to provide a zeolite replicate of the carbon host resulted in very fragile replicas which were of no practical use. The present invention provides a range of approaches by which more robust zeolite replicas can be produced.

The zeolite may be formed on a substrate at a loading of greater than 30% by weight or even greater than 40% by weight, but fragility is increased with lower loading levels hence loading are typically above 15% or even 22% to reduce fragility. Generally, the loading of the zeolite on the substrate does not exceed 50% by weight, although higher loadings are in the scope of the invention. Loading can be increased by increasing the time that the substrate rests in the synthesising solution.

According to a second aspect of the invention, there is provided a composite material. Very surprisingly, it has been found that two different kinds of zeolite can be formed on the carbon substrate. Although particular reference is made to the formation of zeolite LTA, zeolite X, zeolite Y and zeolite H-Sodalite, other aluminosilicates zeolites, might conceivably be incorporated within the composite material (such as, MFI and ZK5).

According to a third aspect of the invention, there is provided a composite material.

The ion exchange zeolite may include a metal cation such as Li, Na, Ca, Mg, K, Al, Sn, a transition metal cation such as Ti, Ag, or a Lanthanide cation.

According to a fourth aspect of the invention, there is provided a method of manufacturing a zeolite.

According to a fifth aspect of the invention, there is provided a method of manufacturing a composite material.

The zeolites may be formed on the substrate by reacting a sodium aluminate containing solution with a sodium silicate containing solution. However, the use of other materials, such as TEOS (Tetraethylorthosilicate), Ludox®, aluminium foil, or alternatively, substituting calcium or potassium containing solutions for the sodium containing solutions are within the scope of the invention.

Without wishing to be bound by any particular theory or conjecture, it is believed likely that the formation of a different zeolite in the pores of the carbon substrate is due to a build up of heat and/or pressure in the carbon pores which eventually reaches a higher level than the level achieved externally of the pores. This opens up the possibility of synthesising zeolites which hitherto have been considered impossible or not cost effective or environmentally viable to produce synthetically.

The invention can provide the formation of two or more zeolites using a single synthetic step. However, it may be possible instead to utilise two or more sequential and separate zeolite-forming synthetic steps.

According to a sixth aspect of the invention, there is provided a method of adsorbing a gas.

For the avoidance of doubt, the term "zeolite formed on the substrate" includes reference to zeolite formed within the pores of the substrate.

According to a seventh aspect of the invention, there is provided a composite material.

The carbon substrate may be a synthetic or natural porous carbon material. The porous carbon material may be microporous (<2 nm), meso-porous (2 nm-50 nm) or macro-porous (>50 nm), or possess combinations of these different scales of porosity. A preferred example of a synthetic carbon is MAST® carbon produced by MAST Carbon International Limited (Henley Park, Guildford, UK). Examples of natural carbon materials include coconut husk and woods such as pine, willow and rattan. The carbon material may be activated if desired but unmodified carbon substrate may be used and are generally considered advantageous as they are generally stronger than activated carbons.

The invention may be performed in various ways, and, by way of example only, some specific embodiments will now described in detail, reference made to the accompanying drawings in which:

FIG. 4 shows $^{29}$Si NMR evidence of NaX formation in C pores;

FIG. 5 shows XRD (*a*) data of MastCarbon® carbon and (*b*) NaX zeolite formation in pores of the MastCarbon® carbon;

FIG. 6 shows temperature—programmed desorption of $CO_2$ and $H_2O$ from carbon ($H_2O$ data is above $CO_2$ data on lefthand most side of plot);

FIG. 7 shows temperature—programmed desorption of $CO_2$ and $H_2O$ from NaX ($H_2O$ data is below $CO_2$ data on lefthand most side of plot); and FIG. 8 shows temperature—programmed desorption of $CO_2$ and $H_2O$ from a LTA—NaX/carbon composite ($H_2O$ data is below $CO_2$ data on lefthand most side of plot).

Figure 1:
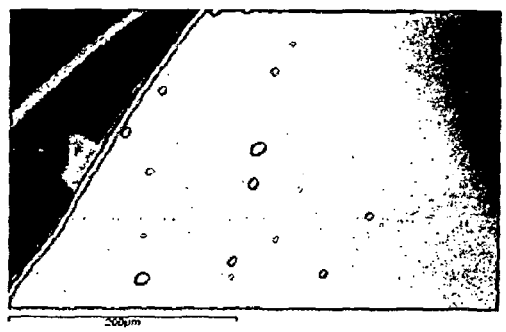
FIG. 1 shows (a) a SEM and (b) an EDX of a silica xerogel support layer and (c) SEM images of the silica support layer as a coating on a carbon sphere.
Figure 1:
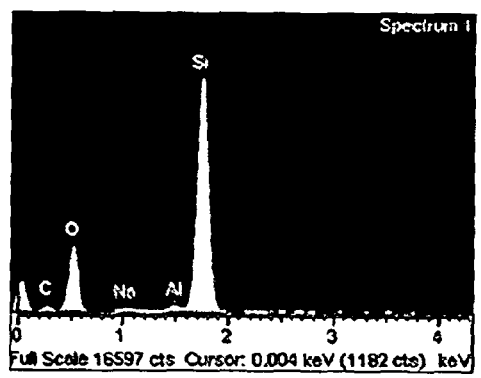
Figure 1:
Figure 1:

Whilst the invention has been described above, it extends to any inventive combination of the features set out above, or in the following description, drawings or claims.

Zeolite Only Monoliths

To increase the strength of the zeolite monoliths, the carbon substrate may be dipped into a colloidal silica to form a silica support layer. Sources include Ludox™ or Tetra ethyl/methyl/propyl ortho silicate (TEOS/TMOS/TPOS), or hybrid/mixtures/combinations of other silanes including but not limited to methyltrimethoxy-silane (MTMS), bis(trimethoxysilyl)ethane (BTMSE), bis(trimethoxysilyl)hexane (BTMSH), and bis(trimethoxysilylpropyl)amine (BTMSPA). Optionally, ethanol may be used to encourage gelation. This coating is then allowed to dry onto the carbon substrate to form a thin, light amorphous silica layer structure. The zeolite can be formed according to the principles described herein, but will sit inside and adhere to the thin silica film.

It is possible that the silica structure/film formed may (due to slight dissolution of the thin film layer) in the highly basic zeolite precursor solution) increase the level of silica content/level of the zeolite at the amorphous silica/zeolite interface, forming a slightly different higher silica to alumina ratio zeolite than required (i.e. forming a slightly different zeolite at the interface). If this is considered a problem, then the amorphous silica dipped carbon substrate can be dipped in a thin solution of a carbon precursor material such as PVA (Polyvinylalcohol), PVAc (Polyvinyl Acetate) or phenolic resin. This is then allowed to dry and can then be used as is, or it can be carbonised to form a protective surface thin film carbon barrier layer over the silica thin film to prevent any dissolution of the silica in the zeolite precursor solution. This carbonisation is usually performed at a temperatures above 200° C., but lower temperatures might be used (thinner films i.e., nanofilms require much lower temperatures. Carbonisation may be in a $N_2$ or $CO_2$ stream, although an oxygen containing stream might also be used, particularly at low temperatures or greater carbon content where carbon does not burn away in a facile manner. The protective surface thin film barrier layer can be removed along with the carbon substrate, for example by carbonisation, leaving only the thin film amorphous silica layer and the zeolite.

The support layer may be silica but may instead be formed using alumina precursors to form a thin film alumina layer and/or clay materials or a combined alumina-silicate layer amorphous layer.

Examples of silica sources include:
1) Colloidal silica (Ludox™) all AM (Aluminium modified) or TM (Titanium modified) or mixtures/hybrid/ratios of.
2) Sodium metasilicate and all hydrates thereof (e.g. sodium metasilicate pentahydrate, nonahydrate etc. or mixtures/hybrid/ratios of other metasilicates, pentahydrate, nonahydrate etc.)
3) TEOS and all other silane precursors or mixtures/hybrid/ratio precursors (TMOS, TEOS, TPOS or others including but not limited to methyltrimethoxy-silane (MTMS), bis(trimethoxysilyl)ethane (BTMSE), bis(trimethoxysilyl)hexane (BTMSH), and bis(trimethoxysilylpropyl)amine (BTMSPA)).
4) All dissolvable silica glass substrate as a precursor or mixtures of. Other silica sources/precursors may be used, and/or mixtures of the above 1)-4) silica precursors in any suitable ratio as an precursor for a thin film silica or as a starter material for an amorphous or crystalline alumina-silicate.

Examples of aluminium sources include:
1) Aluminium tert-sec-butoxide (or any other Aluminium butoxide or mixtures/hybrid/ratios thereof)
2) Sodium Aluminate (or any other metal aluminate or mixtures/hybrid/ratios of sodium and other aluminate)
3) Aluminium hydroxide or boehmite (or any other metal hydroxide or mixtures/hybrid/ratios of aluminium and other hydroxide)
4) Aluminium foil as an aluminium precursor and or other foils and ratio/mixtures of)
5) Aluminium sulphate (or any other metal sulphate or mixtures/hybrid/ratios of aluminium and other sulphate), aluminium nitrate or aluminium chloride.

Other aluminium sources/precursor may be used, and/or mixtures of the above 1)-5) aluminium precursors in any suitable ratio as an precursor for an alumina thin film or as a starter material for an amorphous or crystalline alumina-silicate thin film.

A clay may be used as the support layer or to form the support layer.

Amorphous or crystalline aluminosilicate thin films—or possible combinations of sources of aluminosilicate thin films-may be used as the support layer. Examples of possible precursors include: Ludox™ and Al hydroxide; Na Metasilicate and Al hydroxide; TEOS (or others such as TMOS etc.) and Al hydroxide; Ludox and Al butoxide; Na metasilicate and Al butoxide; TEOS (or others such as TMOS etc.) and Al butoxide; Ludox and Na aluminate; Na metasilicate and Na aluminate; and TEOS (or others TMOS etc.) and Na aluminate. Aluminium-based support layer may also be coated with a carbon precursor material such as PVA (polyvinylalcohol), PVAc (polyvinyl acetate), phenolic resin, a sugar or a carbohydrate from solution. This is then allowed to dry and can be carbonised at a suitable temperature to form a protective surface thin film carbon barrier layer over the thin film to prevent any dissolution thereof.

In known zeolite synthesis methodologies it is common to add templating agents such as TMAH. TEAH, TPAOH (Tetramethyl(ethyl/propyl)ammonium hydroxide) and to use NaOH, NaCl, $HNO_3$, $H_2SO_4$, HCL, Ethanol and SDS (Na dodecylbenzen-sulfonate) as structure determining, templating agents and or starter solvent materials. The use of such substances is within the scope of the invention. However, these substances are corrosive and toxic, and (despite the odd exception detailed below) have not been found to assist in the working of the present invention (although the addition of TMAH to zeolite synthesising solutions can increase adsorption of gases such as hydrofluorocarbons). However, it is considered to be advantageous that the present invention does not normally require the use of these substances.

Synthesis Method:

First stage: The carbon substrate (either natural or synthetic) is dipped into Ludox™ AM 30 wt % colloidal silica (or TEOS) to form a silica gel/film which dries (overnight to a few days at room temperature) to form a silica thin film on the carbon substrate. Adding ethanol and water can assist the gelation process resulting in the formation of a thicker, more porous film. However, the structure can shrink to a greater extent and so is more liable to crack on drying. A preferred ratio is 9 ml ethanol, 1 ml distilled water, 1 ml Ludox. Advantageously this is carried out by mixing the Ludox and water, then pre-dipping the carbon monolith before dipping in the ethanol to gel. HCl and NaOH may be used to slow down or speed up, respectively, the gelation process.

c) It is possible that any zeolites formed onto the substrate will have a d) higher silica ratio when formed near the thin film silica interface and so a second stage can be performed if desired before zeolite is synthesised within the substrate.

Second stage: The whole structure (carbon and silica coat) can then be dipped into a Poly vinyl alcohol (PVA) solution. This solution (20 g PVA to 400 ml 65° C. water and stirred for 15 minutes then filtered) forms a thin PVA coat onto the substrate which is then carbonised in the absence of oxygen to form a thin carbon film on top of the thin silica film.

Third Stage The specific zeolite required can be formed in the pores of the carbon/thin film substrate using either the Thomson or the Charnell recipes (or a combination of the two). However, zeolites can be synthesised using precursors such as Ludox colloidal silica, Na metasilicate, TEOS, Al Butoxide, Na Aluminate, Al hydroxide, Al foil and many combinations thereof as well as HCl, NaOH to slow down/ speed up the gelation process and TMAH, TPAOH templating agents with seeding and/or structure directing agents (SDA) such as HF etc. The Thomson recipe was preferred in the present example as no toxic, environmentally unacceptable chemicals were needed.

Zeolite 4A (LTA) was synthesised by a hydrothermal route as follows: To 84 g deionised water 0.723 g NaOH was added and the solution split into 2× polypropylene containers (42 g×2). 8.2 g of Na Aluminate was dissolved in one of the containers and 15.48 g of Na metasilicate dissolved in the other. The substrate (carbon silica/PVA carbon thin film material) is then placed into the Na metasilicate soln. then removed and quickly placed into the Na Aluminate soln.

The rest of the Na metasilicate is quickly poured into the Na Aluminate container and the mixture is shaken vigorously for 5 minutes (sonicating it is even better and forms sharper structured crystals in the pores). The solution and substrate is left to age overnight and then the polypropylene vessel containing the soln and substrate heated at 99° C.+/−1° C. in a silicon oil bath or oven overnight. Samples are then washed in deionised water and oven dried at 100° C. The carbon is then burnt off at c. 350° C. (150-1000° C. is possible) leaving a zeolite monolithic replica of the carbon template.

To form NaX the synthesis method is identical but the solution ratios are chosen to give a silica rich ratio. 0.723 g of NaOH is dissolved in 168 g of deionised water and this split into two×84 g pots. To one pot 8.2 g of Na Aluminate was added and to the other 30.96 g-38.70 g of Na metasilicate (depends on the silica ratio of NaX desired). The rest of the synthesis is as above for NaA/LTA/4A synthesis.

Figure 3:
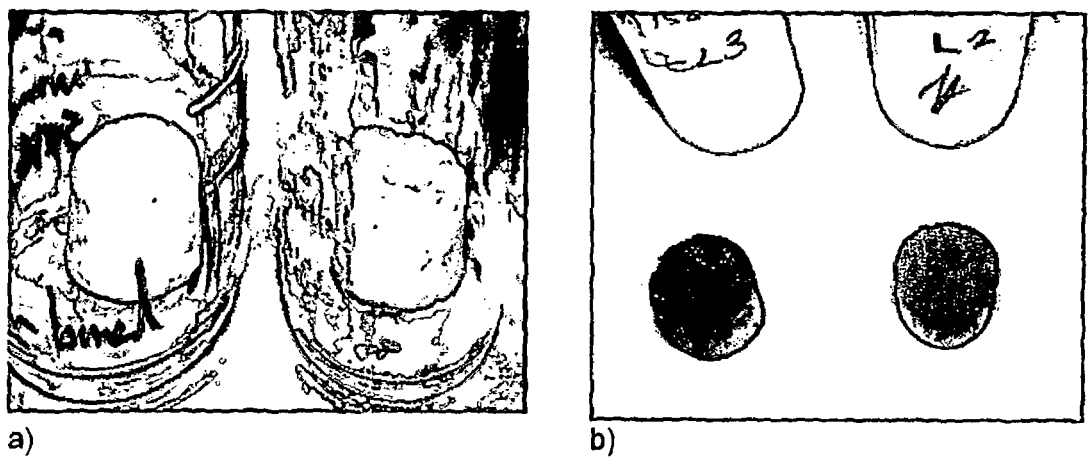
FIG. 3 shows (a) a photograph of silica monoliths and (b) a photograph of carbon monoliths with a thin silica film formed thereon.

The carbon substrate can be burned off before synthesis of zeolite onto the thin film structure if preferred, but the structure is likely to be much heavier and denser due to increased zeolite loading. Also Ludox sol-gel structures can be formed without the carbon inside glassware (with or without pore formers such as ethylene glycol, carbon beads etc.), and once these light porous structures are dried and the organics burnt off, the zeolites can be synthesised directly thereon. FIG. 3 shows such structures. See FIG. 3a left hand silica monolith created from Ludox/ethanol (carbon spheres removed) and FIG. 3a. right Ludox/Ethanol after removal of ethylene glycol. Alternatively the carbon monoliths can be dipped to form a thin silica film (FIG. 3b. left ethanol/Ludox dipped carbon and FIG. 3b. right Ludox only dipped carbon, dried before carbon removal). These are also denser than the structures formed around the carbon substrate and carbon subsequently burned of.

One possible support layer a silica xerogel, was assessed using SEM and EDX (see FIG. 1a .SEM and b.EDX) before being used as a membrane to coat a MASTcarbon™ sphere (FIG. 1c. scale 60 um and d. scale 10 um).

Figure 2:
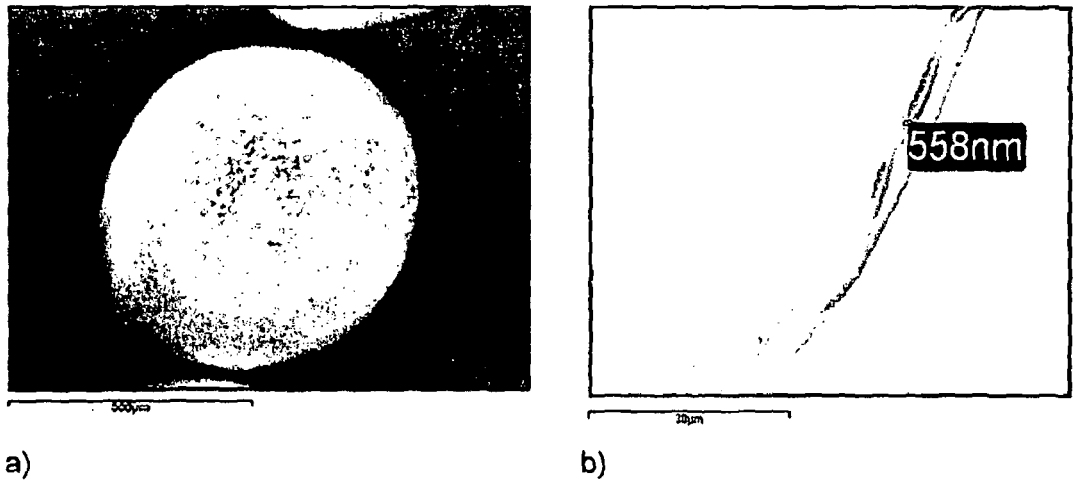
FIG. 2 shows (a) a SEM image of a PVA coated and carbonised zeolite pellet, (b) a SEM image of the PVA coating prior to carbonisation and (c) TGA results of the carbonised PVA coating.
Figure 2:
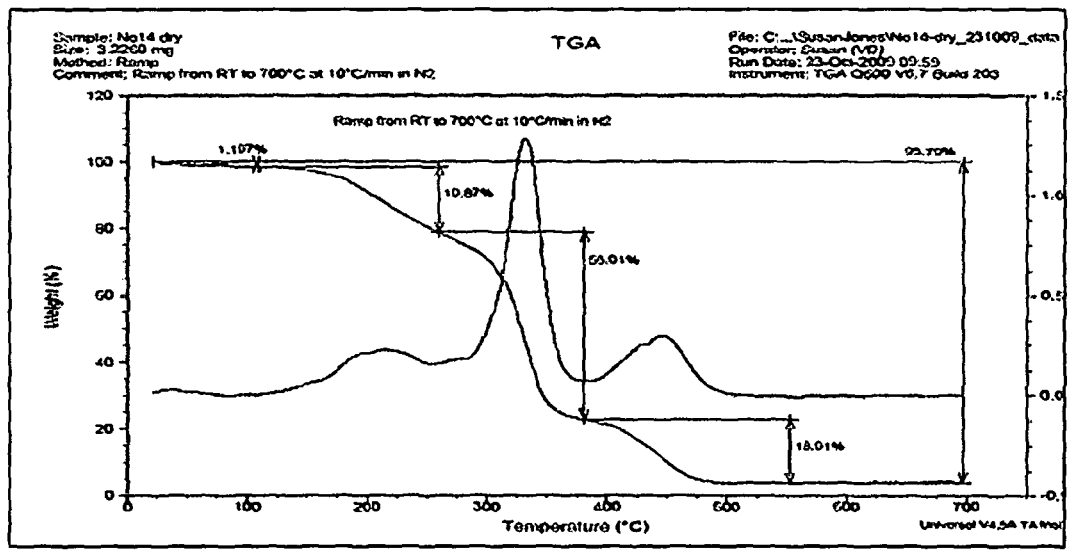

The PVA carbon layer thickness was assessed by coating a zeolite pellet (FIG. 2a.) and as a PVA thin film (FIG. 2b.). TGA results (FIG. 2c.) suggest that carbonisation of a (1% in soln) PVA layer leaves a carbon film c. 23 nm thick, as the film is reduced by 96% on carbonisation and microscopy illustrates that the PVA is only reduced in thickness not length/ width over the coated substrate.

Production of More than One Zeolite on a Porous Carbon Substrate

Zeolites synthesised in the pores of carbon form at a different speed to those synthesised in the external channels and synthesis solution. Powder XRD (X-ray diffraction) and Silicon 29 Magic Angle Spinning—Nuclear Magnetic Resonance $^{29}$Si (Si MAS-NMR) samples taken from the synthesis fluid on an hourly basis confirm that though in the initial stages the zeolite forms in the carbon pores more slowly than in the external solution and channels, the zeolite synthesis continues in the carbon pores after it has been arrested on the external channels and solution. This interesting phenomenon (which is probably due to heat and pressure building up more slowly in the carbon pores but eventually reaching a higher level than externally) allows two or more different zeolites to be synthesised in a single carbon substrate. For instance H-SOD (hydroxy sodalite) was formed in the carbon pores while zeolite 4A/NaA/LTA is formed on the outer channels of the carbon substrate. Therefore the more extreme porous environment within the pores may allow for synthesis of zeolites that are known to exist naturally and/or have hitherto been considered impossible too cost or environmentally inviable to produce synthetically. The multiple zeolite composite material and/or possible new synthetic zeolite structures may be suitable as $H_2$, or $H_2$ precursor storage materials (such as $NH_3$) used as greenhouse/global warming potential (GWP) gas adsorbers, (e.g. $CO_2$, R134a, $CH_4$, water vapour etc.,) for carbon sequestration or for production of syn-gas from CO or $CO_2$ precursors onto these catalytic materials, or to select, adsorb and concentrate biomarkers for numerous applications including breath analysis and electronic nose studies.

Synthesis method: LTA and H-SOD in the pores of carbon. Dissolved 8.2 g of Na Aluminate in 144 g of deionised water with 0.723 g NaOH added (can add 16 g of TEA at this stage if required) then the solution was filtered 7 g of Ludox colloidal (30 wt % AM) silica added. Alternatively the 144 g of water can be split into two equal portions and 15.48 g of Na Metasilicate added to one while the 8.2 g of Na Aluminate added to the other (in place of the colloidal silica). Once again 16 g of TEA can be added—but this should be split equally between the Aluminate and the metasilicate pots. The samples are then shaken or sonicated and left to age at room temperature (from a few hours to 4 days) before being heated at 80-85° C. in an oven for 3-5 weeks. The long synthesis time may be necessary in order to drive the LTA zeolite one step further to H-SOD. Otherwise a synthesis of a few months could be required for some zeolites at very low temperatures such as around 25° C. Alternatively it may be possible to use high temperatures such as 120° C. or above, in which instance a shorter reaction time, from a few hours to days, might be possible.

Once one zeolite is synthesised in the pores a second zeolite can also be synthesised in a second synthesis step also producing two or more zeolites in the carbon pores but though this also produces two or more zeolites within the carbon this is unlikely to produce difficult to synthesis zeolites. A synthetic method utilising a sequential synthetic scheme will now be described. Four carbon substrates were selected: three natural (willow, rattan and pine) and one synthetic (MastCarbon®). All were successful in permitting zeolite synthesis within their pores. Two zeolites were synthesized sequentially in these unmodified C mesopores using different precursor solution Si:Al ratios:

NaX: $Na_{86}[(AlO_2)_{86}.(SiO_2)_{106}].264H_2O$

LTA; $Na_{12}[(AlO_2)_{12}.(SiO_2)_{12}].27H_2O$

Thus NaX or LTA were synthesized in-situ in the un-modified mesopores of the carbon by immersion in $NaOH/NaAlO_2$ aluminate aqueous solution and then $NaOH/Na_2SiO_3$ metasilicate aqueous solution of different ratios and strengths for different lengths of time (with and without a template (e.g. TMAH)). Indeed we believe that the functional groups on the surface of the mesopores in the carbon were themselves templating the nucleating zeolites crystallites. There were seen to be advantages of using unmodified carbons in terms of minimizing cost and damage to the host integrity. Zeolite growth was slower in the C pores than in the bulk solution (as illustrated by $^{29}Si$ NMR that revealed the kinetics of zeolite synthesis therein; see FIG. 4). After drying, XRD confirmed that one of the zeolites had been synthesized (and their average crystallite size) (see FIG. 5).

Ion Exchange

Zeolites, often known as molecular sieves, sieve molecules by size, shape and polarity. The cavity size of the zeolite is therefore key to molecular adsorption and zeolite cavity size can be 'tuned' by ion exchanging. Zeolite 4A (Na+A) becomes 3A when the Na+ ion exchanges with the larger K+, but exchanging for a Ca++ changes the cavity size to 5A due to the fact that only one Ca++ is needed to exchange with two Na+. Hence, with careful tailoring the zeolites can be tuned to adsorb a particular size and/or, shape molecule. Literature suggests that Ag+ LTA and Li+X zeolites are much better adsorbers of $N_2$ than the CaA (zeolite 5A) currently in use in Oxygen Enriched Air Systems (OEA). Therefore, large and cumbersome OEA pressure swing adsorption (PSA) systems could be made much smaller and more portable by changing the zeolite adsorption materials inside them. However, due to their small particle size, the ion exchange of zeolites is not always as straightforward as the literature would suggest. To allow access to the whole surface area of zeolite and prevent the zeolite clumping together, the zeolite crystals must be agitated and often the solution heated (to vibrate ring oxygens in order to allow access to the exchanging ions). When zeolites are held inside the pores of a carbon substrate, ion exchange is a much easier process, as fluid transport to the zeolite is greatly enhanced and the small particle sized zeolite crystals held securely inside the carbon cannot clog up the system. A further advantage is that the innocuous carbon coat allows use of the ion exchange zeolite properties in wastewater and other polluted water ways, rivers and ocean sensing/clean up etc. by exchanging the Na+ in the zeolite for more toxic ions (such as, but not limited to, Ti or Ag cations or Pb or even radioactive cations) whilst preventing the solid acid catalyst zeolite crystals from causing harm to aquatic creatures, small land species and humans as inhaled/ingested particulate matter. The carbon substrate facilitates ease of placement and removal of the zeolite when adsorption is complete allows for easier assessment and recovery of the ions adsorbed and the carbon coat, as mentioned, is non-toxic so safe for most sea life. Light sensitive ions such as Ag cations remain stable for longer inside the dark carbon interior allowing for a more accurate assessment of toxic Ag nano-particulates and their by-products. The carbon coat can also be electrically heated using the resistivity of the carbon to regenerate the composite in order to assess any gases adsorbed. This allows for use as a gas sensor material and also allows for medical use for example as smaller (pocket sized) OEA systems (possibly battery operated temperature/pressure swing adsorption (T/PSA) systems) and other medical applications such as breath analysis biomarker concentrators. Other possible medical uses of the material are expected due to the safety and bio-compatibility of the coat (such as dialysis materials etc).

Ion Exchanging:

H+ exchange is probably the easiest of the ion exchange processes for zeolite materials and involves either copious washing in deionised water or titrating the zeolite while in deionised water with HCl and monitoring the pH. At pH 3 the exchange is considered complete and any further reduction of pH results in complete collapse of the zeolite structure.

The sample must be well washed before ion exchange is commenced. Because when zeolite A is placed in deionised water there is a displacement reaction see below:

$$Na_2A + 2H^+(OH) \longleftrightarrow H_2A + 2Na^+(OH)$$

Therefore pH rises to between 10-11 indicating that H+ ions from water are displacing Na+. With copious washing the zeolite will eventually reach pH 3 but this is laborious and time consuming. Therefore, HCl can be used to speed up the process. This also produces harmless salt (NaCl) rather than NaOH.

Experimental:

4 g of 4A zeolite in 60 g water gave an equilibrium pH of 10.5. Addition of HCl 0.121M by titration was performed until the pH meter indicated pH 3.8. No further addition of the acid gave a lower pH (this was the lowest pH normally recorded even during full zeolite structural collapse. The material was dried and an XRD ran to check the structure was still intact after the exchange.

When the zeolites are held in the pores of carbon, ion exchange can easily be performed just by pouring deionised water through the materials held in an ion exchange column.

Li exchange: A theoretical 100% exchange rate was calculated using the ratio/%/and wt of the zeolite, expected level of Na+ in the zeolite and calculating how much Li+ would be required to exchange fully with the Na+. Ion exchange was performed at 65° C. The zeolite samples were exchanged with $LiNO_3$, and assessed using Atomic Adsorption Spectroscopy (AAS). A composite prepared from Willow carbon and LTA zeolite had an uptake of Li of 0.33 mg per g of zeolite, which was substantially higher than the Li uptake exhibited by Sigma 4A zeolite with no carbon substrate (0.25 mg per g of zeolite). Blank Willow sample did not take up any Li.

Silver exchange: experiments were performed at 25° C. A 20 ppm solution of Ag+ (ICP-MS standard) in Nitric Acid was used to ensure a linear AAS response. Samples of zeolite 4A and LTA only (ie, with no carbon substrate) gave uptake results of 4361-4860 ug of Ag per gram of zeolite. Experiments were also performed on willow/LTA composite samples and a MAST/LTA composite sample, and the content of zeolite in the composite was taken into account to derive uptake values of Ag per gram of zeolite. Values of 9480 and 8929 ug of Ag per gram of LTA zeolite were found for the willow/LTA and MAST/LTA composites, respectively. It is believed that ion exchange is facilitated by the carbon host either due to the increased fluid transport to the zeolite or because the results are less likely to be compromised due to reduced light exposure as the Ag+ ions exchange in and out of the zeolite in equilibrium within the dark carbon host. An initial assessment of the carbon substrates using SEM-EDX found no Ag on the carbon substrate, suggesting that the results are not affected by Ag adsorption onto the substrate.

Adsorption

Carbon Dioxide

Carbon and zeolites both adsorb $CO_2$; but zeolite NaX has been shown in numerous experimental studies to have the best adsorption of $CO_2$ for applications at moderate temperatures (<573K) and atmospheric pressure. However, most researchers are under the impression that NaX adsorption is affected by water vapour. To address these issues and also to make sure that water vapour is adsorbed (as it is also a greenhouse gas and responsible for more global warming pollution than $CO_2$) a combination of zeolite composites was assessed for ambient temperature pressure adsorption of water vapour and $CO_2$ from air. In the experimental work performed to assess $CO_2$ adsorption, unconditioned NaX zeolite does not appear to desorb $CO_2$ below 633K. The MAST™ carbon did (in this work) desorb $CO_2$, but preferentially desorbed $H_2O$ below 373K. A composite of LTA-Carbon desorbed $CO_2$ in preference to $H_2O$ at higher temperatures (448K) but desorbed both $H_2O$ and $CO_2$ below 373K. NaX-Carbon composites release both simultaneously. From an initial analysis it appeared that it is only by combining the composites of NaX-Carbon and LTA-Carbon in succession that $CO_2$ and $H_2O$ are desorbed at different rates. It is possible that as the Carbon and LTA zeolite desorb $CO_2$ and $H_2O$ simultaneously the $H_2O$ is readsorbed by the zeolite and so $CO_2$ alone is desorbed/produced below 373K (when LTA/NaX and carbon are combined).

Further experiments used LTA and NaX zeolites. These zeolites were selected because NaX desorbs $H_2O$ at lower temperatures than $CO_2$ and LTA desorbs $CO_2$ at lower temperatures than $H_2O$. The adsorption properties of carbon (FIG. 6), NaX zeolite (FIG. 7), and sequentially grown NaX/LTA/carbon composites (FIG. 8) were investigated. The predried composites (373K) were allowed to adsorb $CO_2$ and $H_2O$ from the atmosphere at 16 h at 293K. Mass spectrometry-residual gas analysis (RGA) (at m/z=44 and 18) was used to follow the rate of release/desorption of $CO_2$ and $H_2O$ into a $N_2$ stream (22 ml/min) during heating from 295-633K.

The separation of $H_2O$ and $CO_2$ could be important in some scientific processes (such as flue gas stream adsorption and desorption) and it may be possible to use a tandem arrangement of zeolite/carbon composites tailored to adsorb and then TPD at discrete temperatures to separate and concentrate flue gases and/or environmental pollutants (such as $SO_x$, $NO_x$, $CH_4$, $CO_2$ and $H_2O$ vapour) for use as separation and adsorption process materials.

Ammonia

Table 1 gives critical data for a number of samples in terms of $NH_3$ temperature programmed desorption (TPD). In summary, it is clear that on a unit weight basis NaX adsorbs/desorbs more $NH_3$ than C, but that NaX in the MAST™/NaX (no TMAH) composite adsorbs/desorbs a similar amount of $NH_3$ to NaX alone. This means that the NaX within the C is accessible and for a basic molecular probe is similar to the NaX prepared traditionally. An interesting possibility is to use one or more carbon-zeolite composites to adsorb both carbon dioxide and ammonia (or water) as a hydrogen precursor, for example to serve as syn-gas reactants in a useful reaction (water-gas shift, Fischer-Tropsch etc. to convert emissions to fuel, using the catalytic zeolite to reduce the thermodynamic barriers to such conversations).

TABLE 1

$NH_3$ TPD

| Sample | $S_{BET}$ (m$^2$/g) Surface Area | μmol/g | $T_{max}$ (K) $NH_3$ | $E_a$ (kJ/mol) | $T_{max}$ (K) $H_2O$ |
|---|---|---|---|---|---|
| NaX (10 h) | 846 | 18620 | 393-420 | 61 | 550 |
| NaX 2$^{nd}$ after TPD | 846 | 15050 | 420 | 53 | 550 |
| MAST/NaX (22% NaX) | 507 | 3696 (16818) | 351-480 | 62 | 550 |
| MAST/NaX(TMAH) (28% NaX) | 523 | 1583 (5654) | 360-420 | 78 | 500 |
| MAST/NaX(TMAH) 2$^{nd}$ after TPD | 523 | 1859 (6639) | 368-402 | 50 | 500 |
| MAST | 535 | 292 | 322 | 80 | 322 |

( ) bracketed data is per g NaX 1,1,1,2 Tetrafluoroethane (HFC-134a)

Table 2 gives critical data for HFC-134a adsorption-desorption on a number of samples. Interestingly, it is clear that on a unit weight basis MAST/NaX(TMAH) adsorbs-desorbs more HFC-134a than NaX(no TMAH) (and much more than the C substrate alone).

TABLE 2

HFC-134a TPD

| Sample | $S_{BET}$ (m$^2$/g) Surface Area | μmol/g* | $T_{max}$ (K) $NH_3$ | $E_a$ (kJ/mol) | $T_{max}$ (K) $H_2O$ |
|---|---|---|---|---|---|
| NaX (10 h) | 846 | 1195 | 348 | 140 | >375 |
| MAST/NaX(TMAH) (28% NaX) | 523 | 457 (1632) | 358 | 100 | >410 |
| Carbonised MAST | 535 | 7.7 | 330-350 | 145 | 340 |

*at 298 K and p/p$_o$ = 0.30 ( ) bracketed data is per g NaX.
Note:
MAST/NaX was not taken to saturation point, hence adsorption is expected to be even higher.

The invention claimed is:

1. A composite material comprising a porous carbon substrate and an ion exchanged zeolite formed on the substrate, or a porous exchanged zeolite produced from said composite material by substantially or completely removing said substrate, wherein the ion exchanged zeolite is one of zeolite LTA, zeolite X, zeolite Y, or zeolite H-Sodalite.

2. A composite material comprising a porous carbon substrate and an ion exchanged zeolite formed on the substrate, or a porous exchanged zeolite produced from said composite material by substantially or completely removing said substrate, wherein the ion-exchanged zeolite comprises Ag or Li cations.

3. A composite material comprising a porous carbon substrate and an ion exchanged zeolite formed on the substrate, or a porous exchanged zeolite produced from said composite material by substantially or completely removing said substrate, wherein the ion exchanged zeolite is Ag$^+$ LTA, Li$^+$X or H$^+$LTA/X.

4. A composite material comprising a porous carbon substrate and an ion exchanged zeolite formed on the substrate, or a porous exchanged zeolite produced from said composite material by substantially or completely removing said substrate, wherein the ion exchanged zeolite comprises a metal cation.

5. A method of adsorbing a gas comprising the steps of:
providing a composite material including a porous carbon substrate and a zeolite formed on the porous carbon substrate, or a zeolite produced from said composite material by substantially or completely removing said substrate; and
exposing the composite material or zeolite to the gas so that the gas is adsorbed by at least the zeolite;
wherein the gas is carbon monoxide, carbon dioxide, a hydrofluorocarbon, ammonia, water vapor or methane.

6. A method according to claim 5, wherein the hydrofluorocarbon is 1,1,1,2 tetrafluoroethane.

7. A method according to claim 5, wherein the composite material or zeolite is exposed to carbon dioxide and ammonia and/or water vapor so that carbon dioxide and ammonia and/or water vapor are adsorbed by at least the zeolite.

8. A method according to claim 5, wherein the composite material or zeolite is exposed to carbon monoxide and ammonia and/or water vapor so that carbon monoxide and ammonia and/or water vapor are adsorbed by at least the zeolite.

* * * * *